United States Patent
Hayman et al.

(10) Patent No.: US 8,235,941 B2
(45) Date of Patent: Aug. 7, 2012

(54) OCCLUSION CATHETER HAVING COMPLIANT BALLOON FOR USE WITH COMPLEX VASCULATURE

(75) Inventors: Douglas Ray Hayman, Mission Viejo, CA (US); Peter Gregory Davis, Dana Point, CA (US); Maria De Jesus Sanson, San Clemente, CA (US); Komonn Lim Reedy, Tustin, CA (US); Todd Jeffrey Hewitt, Laguna Niguel, CA (US)

(73) Assignee: Tyco Healthcare Group LP, Mansfield, MA (US)

( * ) Notice: Subject to any disclaimer, the term of this patent is extended or adjusted under 35 U.S.C. 154(b) by 56 days.

(21) Appl. No.: 11/868,049

(22) Filed: Oct. 5, 2007

(65) Prior Publication Data
US 2008/0027378 A1 Jan. 31, 2008

Related U.S. Application Data

(62) Division of application No. 10/235,064, filed on Sep. 4, 2002.

(60) Provisional application No. 60/317,232, filed on Sep. 4, 2001, provisional application No. 60/318,215, filed on Sep. 7, 2001.

(51) Int. Cl.
*A61M 31/00* (2006.01)
*A61M 37/00* (2006.01)

(52) U.S. Cl. .............................. 604/103.06; 604/103.07

(58) Field of Classification Search ............. 604/103.06, 604/103.07, 103.1
See application file for complete search history.

(56) References Cited

U.S. PATENT DOCUMENTS

| | | | |
|---|---|---|---|
| 5,458,568 A | 10/1995 | Racchini et al. | |
| 5,580,568 A | 12/1996 | Greff et al. | |
| 5,667,767 A | 9/1997 | Greff et al. | |
| 5,695,480 A | 12/1997 | Evans et al. | |
| 5,702,361 A | 12/1997 | Evans et al. | |
| 5,795,331 A | 8/1998 | Cragg et al. | |
| 5,830,178 A | 11/1998 | Jones et al. | |
| 5,928,260 A | 7/1999 | Chin et al. | |
| 6,007,573 A | 12/1999 | Wallace et al. | |

(Continued)

FOREIGN PATENT DOCUMENTS
EP 0241038 A2 10/1987
(Continued)

OTHER PUBLICATIONS

Castaneda-Zuniga et al., "Interventional Radiology in Vascular Embolotherapy," Part 1, 1:9-32, Williams & Wilkins, Publishers (1992).

(Continued)

*Primary Examiner* — Nicholas Lucchesi
*Assistant Examiner* — Rebecca E Eisenberg
(74) *Attorney, Agent, or Firm* — Elizabeth A. O'Brien, Esq

(57) ABSTRACT

A catheter used for treatment of complex vasculature, such as a bifurcated aneurysm, is provided with an inflatable balloon at a distal portion thereof. The shape, location and material of the inflatable balloon are selected such that when inflated, the balloon conforms to the shape of the complex vasculature, or at least a portion thereof, without appreciably deforming the vessel walls. In this manner, the balloon can be used to control flow in the vasculature, for example occluding a selected branch of the vasculature during introduction of material in order concentrate the material and minimize its disbursement by blood flow.

16 Claims, 1 Drawing Sheet

U.S. PATENT DOCUMENTS

| | | | |
|---|---|---|---|
| 6,017,977 | A | 1/2000 | Evans et al. |
| 6,048,333 | A * | 4/2000 | Lennox et al. ............ 604/113 |
| 6,096,021 | A | 8/2000 | Helm et al. |
| 6,254,628 | B1 | 7/2001 | Wallace et al. |
| 6,531,111 | B1 | 3/2003 | Whalen et al. |
| 6,544,217 | B1 * | 4/2003 | Gulachenski ............ 604/96.01 |
| 6,645,167 | B1 | 11/2003 | Whalen et al. |
| 2003/0060756 | A1 | 3/2003 | Hayman et al. |

FOREIGN PATENT DOCUMENTS

| | | |
|---|---|---|
| WO | WO 98/26832 | 6/1998 |
| WO | WO 00/71197 | 11/2000 |

OTHER PUBLICATIONS

Kinugasa et al., "Direct Thrombosis of Aneurysms with Cellulose Acetate Polymer, Part II—Preliminary Clinical Experience," J. Neurosurg., 77:501-507 (1992).

Kinugasa et al., "Cellulose Acetate Polymer Thrombosis for the emergency Treatment of Aneurysms: Angiographic Findings, Clinical Experience, and Histopathological Study," Neurosurgery, 34:694-701 (1994).

Mandai et al., "Direct Thrombosis of Aneurysms with Cellulose Acetate Polymer: Part I—Results of Thrombosis in Experimental Aneurysms," J. Neurosurg., 77:497-500 (1992).

Szikora, et al., Endovascular Treatment of Experimental Aneurysms with Liquid Polymers: The Protective Potential of Stents, Neurosurgery, 38(2):339-347 (1996).

Talia, et al., "Bioabsorbable and Biodegradable Stents in Urology," J. Endourology, 11(6):391 (1997).

International Examination Report from EP Application No. 10 01 0337 dated Mar. 20, 2012.

* cited by examiner

OCCLUSION CATHETER HAVING COMPLIANT BALLOON FOR USE WITH COMPLEX VASCULATURE

CROSS-REFERENCE TO RELATED APPLICATIONS

This application is a divisional of Application Publication No. US 2003/0060756, filed Sep. 4, 2002, now pending, which claims priority under 35 U.S.C. §119(e) to U.S. Provisional Applications Ser. Nos. 60/317,232 and 60/318,215, filed Sep. 4, 2001, and Sep. 7, 2001, respectively, the entire contents of all of which are incorporated herein by reference.

BACKGROUND OF THE INVENTION

Field of the Invention

The invention is directed to balloon catheters used in the treatment of aneurysms and other vascular diseases in a mammalian patient.

REFERENCES

The following publications are cited in this application as superscript numbers:
[1] Castaneda-Zuniga, et al., *Interventional Radiology*, in Vascular Embolotherapy, Part 1, 1:9-32, Williams & Wilkins, Publishers (1992).
[2] Greff, et al., Compositions for Use in Embolizing Blood Vessels, U.S. Pat. No. 5,667,767, issued Sep. 16, 1997.
[3] Evans, et al., Cellulose Diacetate Compositions for Use in Embolizing Blood Vessels, U.S. Pat. No. 5,580,568, issued Dec. 3, 1996.
[4] Evans, et al., Novel Embolizing Compositions, U.S. Pat. No. 5,695,480, issued Dec. 9, 1997.
[5] Jones, et al., Methods for Embolizing Vascular Sites with an Embolizing Composition Comprising Dimethylsulfoxide, U.S. Pat. No. 5,830,178, issued Nov. 3, 1998.
[6] Evans, et al., Methods for Embolizing Blood Vessels, U.S. Pat. No. 5,702,361, issued Dec. 30, 1997.
[7] Evans, et al., Methods for Embolizing Blood Vessels, U.S. Pat. No. 6,017,977, issued Jan. 25, 2000.
[8] Wallace, et al., Intracranial Stent and Method of Use, U.S. Pat. No. 6,007,573, issued Dec. 28, 1999.
[9] Racchini, et al., Porous Balloon For Selective Dilation and Drug Delivery, U.S. Pat. No. 5,458,568, issued Oct. 17, 1995.
[10] Whalen, et al., Novel High Viscosity Embolizing Compositions, U.S. Pat. No. 6,531,111, issued Mar. 11, 2003.
[11] Szikora, et al., *Endovascular Treatment of Experimental Aneurysms with Liquid Polymers: The Protective Potential of Stents*, Neurosurgery, 38(2):339-347 (1996).
v[12] Kinugasa, et al., *Direct Thrombosis of Aneurysms with Cellulose Acetate Polymer, Part II-Preliminary Clinical Experience*, J. Neurosurg., 77:501-507 (1992).
[13] Kinugasa, et al., *Cellulose Acetate Polymer Thrombosis for the emergency Treatment of Aneurysms: Angiographic Finding, Clinical Experience, and Histopathological Study*, Neurosurgery, 34:694-701 (1994).
[14] Mandai, et al., *Direct Thrombosis of Aneurysms with Cellulose Acetate Polymer: Part I-Results of Thrombosis in Experimental Aneurysms*, J. Neurosurg., 77:497-500 (1992).
[15] Talia, et al., *Bioabsorbable and Biodegradable Stents in Urology*, J. Endourology, 11(6):391 (1997).
[16] Wallace, et al., Intracranial Stent and Method of Use, U.S. Pat. No. 6,254,628, issued Jul. 3, 2001.

All of the above references are herein incorporated by reference in their entirety to the same extent as if each individual reference was specifically and individually indicated to be incorporated herein by reference in its entirety.

STATE OF THE ART

Aneurysms arise in mammalian subjects and, in particular, human subjects as a result of vascular disease wherein the arterial wall weakens and, under pressure due to blood flow, the arterial wall "balloons." Continued growth and/or eventual rupture of the ballooned arterial wall are associated with high morbidity and mortality rates. Intracranial aneurysms are of particular concern because surgical procedures to treat these aneurysms before rupture are often not feasible and further because rupture of these aneurysms can have devastating results on the patient even if the patient survives rupture. Accordingly, treatment protocols for intracranial aneurysms may be prophylactic in nature, i.e., to inhibit rupture or rerupture of the aneurysm rather than to inhibit bleeding from the ruptured aneurysm.

Methods well documented in the art to inhibit intracranial aneurysmal rupture/bleeding include the delivery into the aneurysmal sac of non-particulate agents such as metal coils which are designed to induce thrombosis after delivery to the aneurysm, thereby inhibiting blood flow into the aneurysm[1]; delivery of a fluid composition into the aneurysmal sac which composition solidifies in the sac to inhibit blood flow into the aneurysm[2-5,10]; or a delivery of a combination of non-particulate agents and a fluidic composition into the aneurysmal sac to inhibit blood flow into the aneurysm[6-7].

In each case, the intracranial aneurysm is treated by filling the aneurysmal sac in a manner which inhibits blood flow into the sac. This reduced blood flow correlates to reductions in aneurysmal stress and, hence, a reduction in the likelihood of rupture. However, care must be taken to ensure against migration of non-particulate agents or fluid composition beyond the aneurysmal sac (which can occur, for example, by overfilling of the sac) because this can result in parent artery or distal embolization which, in turn, has its own high level of morbidity associated therewith[11].

One method of containing the embolizing agent in the aneurysmal sac involves the use of a catheter having an occlusion or attenuation balloon. The catheter, and, specifically, the occlusion/attenuation balloon provided at the distal end thereof, performs the dual functions of blocking or impeding flow in the vessel during treatment, such that embolizing agent migration potential is significantly reduced, and providing a sealing wall or barrier against the neck of the aneurysmal sac, which aids in retaining the embolizing agent within the sac during its introduction.

Because the aneurysmal sac is usually associated with diseased tissue whose structural integrity is therefore compromised, it is important to minimize the exertion of pressure against the vessel. The occlusion balloon, therefore, must be designed to provide proper support against the vessel, conforming to the shape of the vessel and providing the necessary functionality associated with its use, without unduly stressing the tissue. In simple cases, wherein the aneurysmal sac is non-bifurcated and is located in a symmetrical, substantially constant-diameter vessel, this is readily accomplished with conventional balloon designs. However, in more complex vasculature, for example bifurcated, multi-branched or varying-diameter vessels, conventional designs are confronted with challenges which they do not satisfactorily meet. Specifically, these conventional designs utilize balloons, which, when inflated to the limits of safe operation—that is, to levels which do not impart unsustainable tissue deformation—fail to fully conform to the complex vessel shape, and, accordingly, fail to provide the proper amount of flow impedance or occlusion and support against the outflow of embolizing agent during treatment.

BRIEF SUMMARY OF THE INVENTION

In accordance with the invention a microcatheter suitable for temporary vascular occlusion is provided. The microcatheter includes a substantially tubular structure with at least one lumen, and a balloon located at the distal portion of the tubular structure and in fluid communication with the lumen. The balloon is designed to deform at a pressure which is less than the pressure required to deform the vascular wall when placed into a blood vessel.

Further in accordance with the invention, a method for treating an aneurysm in a mammal is provided, wherein the method includes identifying an aneurysm in the mammal, and providing a catheter comprising a substantially tubular structure with at least one lumen and a vascular balloon located at the distal portion of the tubular structure and in fluid communication with the lumen, wherein the balloon deforms at a pressure less than the pressure required to deform the vascular wall in the vicinity of the aneurysm. The catheter is inserted into the blood vessel associated with the aneurysm, wherein the distal portion of said catheter is located at a position such that upon expansion of said balloon blood flow into the aneurysm is either attenuated and/or diverted prior to deformation of the vascular wall. An embolizing agent is delivered into the aneurysm to inhibit blood flow into said aneurysm.

Further in accordance with the invention, a catheter suitable for treating an aneurysm in a vascular wall is provided. The catheter includes a substantially tubular structure having at least one lumen, and an inflatable balloon located at a distal portion of the tubular structure and in fluid communication with the lumen, wherein at least a portion of the inflatable balloon comprises a material which deforms at a pressure which is less than the pressure required to deform the vascular wall containing the aneurysm.

Further in accordance with the invention, a method for treating an aneurysm formed in the vascular wall of a mammalian patient is provided, the aneurysm being formed in the vicinity of at least one lumen defined by a blood vessel associated with the aneurysm. The method includes identifying an aneurysm in the mammalian patient, introducing a balloon into the vicinity of the aneurysm, the balloon being provided on a catheter which comprises a substantially tubular structure having at least one lumen in communication with the balloon, at least a portion of the balloon comprising a material which deforms at a pressure which is less than the pressure required to deform the vascular wall in which the bifurcated aneurysm is formed, inflating the balloon such that blood flow into the aneurysm is attenuated and/or diverted prior to undesired compression of the vascular wall, and delivering into the aneurysm an embolizing agent which inhibits blood flow into said aneurysm.

Further in accordance with the invention, a catheter suitable for use in a complex vessel is provided. The catheter includes a substantially tubular structure having at least one lumen, and an inflatable balloon located at a distal portion of the tubular structure and in fluid communication with the lumen, wherein at least a portion of the inflatable balloon comprises a material which, when the balloon is inflated, conforms to the shape of the vessel for a sufficient length of the vessel to attenuate and/or occlude blood flow therein without significantly deforming the vessel.

BRIEF DESCRIPTION OF THE SEVERAL VIEWS OF THE DRAWING(S)

Many advantages of the present invention will be apparent to those skilled in the art with a reading of this specification in conjunction with the attached drawings, wherein like reference numerals are applied to like elements and wherein.

DETAILED DESCRIPTION OF THE INVENTION

Figure 1:
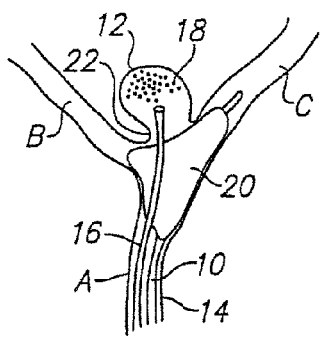
FIG. 1 is a diagrammatical view of the use of the catheter in accordance with the invention during an embolization procedure.

FIG. 1 schematically shows an occlusion catheter 10 in use in the treatment of an aneurysmal sac 12 in accordance with the invention. Blood vessel 14 is complex in shape and structure and is shown as having a main portion A, and as bifurcating into two branches B and C. It will be appreciated that more complex vessel structures, including those having varying diameters, or those having more than two branches, originating from the same or different locations relative to the main portion, can be treated in accordance with the methods and devices of the invention without departure from the spirit or scope of the invention. Blood vessel 14 is a neurological vessel, in accordance with the preferred application of the teachings of the invention.

Also shown in FIG. 1 is an injection catheter 16, depicted in position during treatment of aneurysmal sac 12. Catheter 16 is a separate catheter from catheter 10 and is used to introduce an embolizing agent 18 into the aneurysmal sac 12. The embolizing agent may be a one or more coils (not shown), or it may be a fluid composition, preferably comprising either a biocompatible polymer or a biocompatible prepolymer, but can also be a combination of coils with a fluid composition, as described by Evans[6-7]. When a biocompatible polymer is employed, the fluid composition preferably comprises a biocompatible polymer, and optionally a biocompatible contrast agent, and a biocompatible solvent which solubilizes the biocompatible polymer wherein sufficient amounts of the polymer are employed in the composition such that, upon delivery to the aneurysm, a polymer precipitate forms which fills at least a portion of the aneurysmal sac thereby inhibiting blood flow therein. Preferably, the viscosity of the polymer composition is at least about 150 cSt at 40° C.

Such polymer composition can comprise, for example, a biocompatible polymer at a concentration of from about 2 to 50 weight percent; a biocompatible contrast agent at a concentration of from about 10 to about 40 weight percent; and a biocompatible solvent from about 10 to 88 weight percent wherein the weight percent of the biocompatible polymer, contrast agent and biocompatible solvent is based on the total weight of the complete composition.

Preferably, in this particular composition, the concentration of the polymer ranges from 6 to 50 weight percent and more preferably 8 to 30 weight percent.

Preferably, the polymer composition has a viscosity of at least about 150, preferably at least about 200 and more preferably at least 500 cSt at 40° C. More preferably the viscosity ranges from about 200 to 40,000 cSt at 40° C., more preferably from about 500 to 40,000 cSt at 40° C. The viscosity can also range from about 500 to 5000 cSt at 40° C.

In another aspect of the invention, the biocompatible polymer can be replaced with a biocompatible prepolymer and, when so used, the presence of the biocompatible solvent becomes optional. In a further preferred embodiment, the biocompatible solvent is dimethylsulfoxide (DMSO), ethanol, ethyl lactate or acetone.

The term "biocompatible polymer" refers to polymers which, in the amounts employed, are non-toxic and substantially non-immunogenic when used internally in the patient and which are substantially insoluble in the body fluid of the mammal.

The biocompatible polymer is preferably non-biodegradable. Suitable non-biodegradable biocompatible polymers include, by way of example, cellulose acetates[2-5,10] (including cellulose diacetate), ethylene vinyl alcohol copolymers, hydrogels (e.g., acrylics), polyacrylonitrile, polyvinylacetate, cellulose acetate butyrate, nitrocellulose, copolymers of urethane/carbonate, copolymers of styrene/maleic acid, and mixtures thereof.

Preferably, the biocompatible polymer employed does not cause an adverse inflammatory reaction when employed in vivo. The particular biocompatible polymer employed is selected relative to the viscosity of the resulting polymer solution, the solubility of the biocompatible polymer in the biocompatible solvent, and the like. For example, the selected biocompatible polymer should be soluble in the amounts employed in the selected biocompatible solvent and the resulting composition should have a viscosity suitable for in vivo delivery by, e.g., injection, or by screw-assisted syringe delivery. Such factors are well within the skill of the art.

Preferred biocompatible polymers include cellulose diacetate and ethylene vinyl alcohol copolymer.

Cellulose diacetate polymers are either commercially available or can be prepared by art recognized procedures.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the properties of the composition. Such additional monomers include, by way of example only, maleic anhydride, styrene, propylene, acrylic acid, vinyl acetate and the like.

The term "contrast agent" refers to a biocompatible radiopaque material capable of being monitored during injection into a mammalian subject by, for example, radiography. The contrast agent can be either water soluble or water insoluble and preferably does not contain radioactivity above the native or endogenous amounts naturally occurring in the elements employed (i.e., are "non-radioactive").

Examples of water soluble contrast agents include metrizamide, iopamidol, iothalamate sodium, iohexol, iodomide sodium, and meglumine. Examples of water insoluble contrast agents include tantalum, tantalum oxide, and barium sulfate, each of which is commercially available in the proper form for in vivo use including a preferred particle size of about 10 µm or less. Other water insoluble contrast agents include gold, tungsten, and platinum powders.

Preferably, the contrast agent is water insoluble (i.e., has a water solubility of less than 0.01 mg/ml at 20° C.).

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, acetone, ethyl lactate, and the like. Aqueous mixtures with the biocompatible solvent can also be employed provided that the amount of water employed is sufficiently small that the dissolved polymer precipitates upon contact with the blood. Preferably, the biocompatible solvent is dimethylsulfoxide.

As seen from FIG. 1, catheter 10 is provided with a balloon 20 at a distal portion thereof. Balloon 20, shown in an inflated state, occupies portions of the interior of main portion A, and branches B and C, of vessel 14. In this manner, balloon 20 occludes, or attenuates, flow in vessel 14, such that embolizing agent 18 can be introduced into aneurysmal sac 12 with minimal migration and loss. The size and material of balloon 20, and the inflation pressure applied thereto, are selected such that the balloon conforms to the irregular shape and structure of vessel 14, and provides the necessary flow occlusion and/or attenuation to effectively apply embolizing agent 18, without appreciably deforming or stressing the vessel. Further, by such appropriate selection, balloon 20 can provide an effective barrier against neck 22 of aneurysmal sac 12, such that undesired outflow of embolizing agent 18 from the aneurysmal sac is reduced. All of these factors significantly contribute to the safety and efficacy of the embolization procedure.

Figure 2:
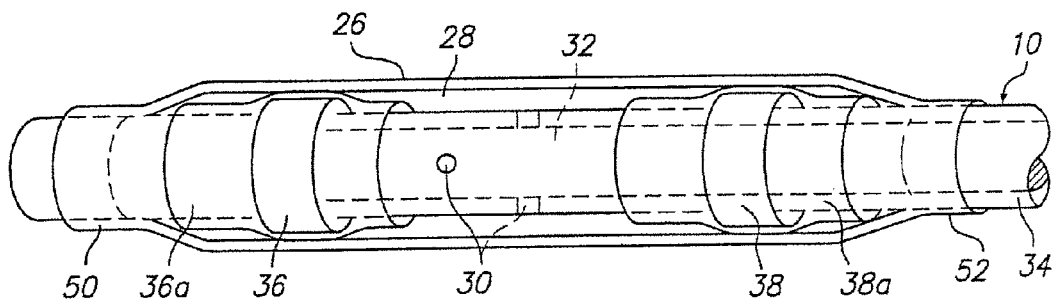
FIG. 2 is a perspective view of a distal portion of a catheter in accordance with the invention.

FIG. 2 shows in greater detail the distal portion of catheter 10 of the invention. The distal portion includes balloon 20, shown in a deflated state, and comprising a layer of flexible balloon material 26 defining a chamber 28. Holes 30 provide fluid communication between chamber 28 and a central lumen 32 extending longitudinally within elongate, generally tubular body 34 of catheter 10.

The distal portion of catheter 10 is also provided with radiopaque marker bands 36 and 38, which are retained in position around body 34 by corresponding marker band retainers 36a and 38a. Retainers 36a and 38a are preferably of a flexible material, such as plastic, which is heat shrunk over markers 36 and 38 during catheter fabrication. It will be appreciated that retainers 36a and 38a can alternatively be made of a single, unitary component extending over markers 36 and 38, in which case it would be provided with holes in registry with holes 30 to facilitate communication between chamber 28 and central lumen 32. Marker bands 36 and 38 may be of metallic or polymeric material, and may alternatively be adhesively bonded in position, rather than using retainers 36a and 38a.

Central lumen 32 is in fluid communication with a fluid reservoir (not shown) at the proximal end of catheter 10. Fluid (not shown) from the reservoir is selectively introduced into chamber 28, via holes 30, in order to inflate balloon 20 during operation. The fluid may be saline and/or a contrast agent injected by syringe (not shown).

Figure 3A:
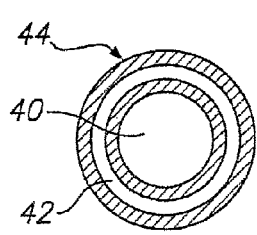
FIGS. 3A and 3B are cross-sectional views of concentric (FIG. 3A) and non-concentric (FIG. 3B) lumen arrangements of catheters in accordance with the invention.
Figure 3B:
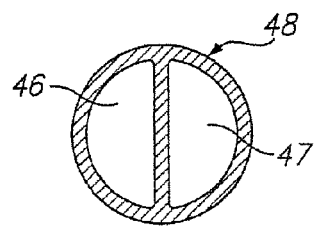

In an alternative structure, the catheter is provided with more than one lumen, at least one of which is in communication with the exterior of catheter 10 at the distal portion of the catheter, such that material can be introduced into or removed from vessel 14, or such that in situ measurements of various patient conditions, such as pressure, can be accurately performed. Moreover, additional lumens may be provided to accommodate a guidewire or a microcather in order to facilitate introduction of the catheter to the target portion of the patient's vasculature, in accordance with known catheterization techniques. Lumen 32 can be adapted for this purpose, such that lumen 32 can serve the multiple purposes of accommodating a guidewire and providing inflation fluid to balloon 20. The multiple lumens can be concentric, or they can extend along different portions of the catheter, as seen from FIGS. 3A and 3B, respectively showing cross-sectional views of multiple lumens 40, 42 and 46, 47 in concentric and non-concentric arrangements in catheters 44 and 48 in accordance with the invention.

Balloon material 26 is selected to be flexible, such that balloon 20, when inflated, is very compliant. Preferably, material 26 is of a composition which is based on styrenic olefinic rubber and hydrogenated isoprene, such as that sold under the trade name ChronoPrene™, available from CT Biomaterials, a division of CardioTech International, Inc. ChronoPrene™ includes the additives polypropylene as a reinforcing agent, and mineral oil as a plasticizer and processing agent. Balloon material 26 is sterilizable and biocompatible, and is compatible with the materials used during the embolization process. In particular, it is compatible with solvents (for example dimethylsulfoxide (DMSO)), polymers, prepolymers and other materials involved in the embolization process. The contemplated thickness of the balloon material 26 is in the range of about 0.004 inches to about 0.006 inches, and is preferably about 0.005 inches.

The characteristics of balloon material 26—including its material, shape, size and the manner in which it is formed and applied relative to tubular body 34—are selected such that balloon 20, when inflated, readily takes the path of least resistance within the blood vessel, and minimally impacts the shape and integrity of the compromised tissue. This reduces the threat of rupture, and of subsequent stenosis. At the same time, the functionally of the balloon is unhindered-that is, the balloon serves to effectively occlude or impede blood flow, or, in some situations, divert it from an existing flow pattern in a bifurcated, complex vessel in a controlled, safe and reliable manner. The balloon 20, or at least a portion thereof, will thus be more deformable than the vascular wall in the vicinity of the aneurysmal sac, even when that vascular wall is diseased and is of compromised strength and stiffness. The balloon 20, or portions thereof, however, will remain sufficiently rigid during operation so as not to appreciably penetrate into the opening, or neck, of the aneurysmal sac, even in situations where the neck of the aneurysmal sack is larger than the opening of a branch of the bifurcated vessel.

Factors to consider in providing the necessary balloon performance are modulus and tensile strength of balloon material 26. A modulus at 300%, having a value less than about 300 psi and/or a tensile strength of about 600 psi, is preferred. ChronoPrene™ 15A can be used, which has a Hardness-Shore A ASTM D2240 (3 sec.) rating of about 15, a specific gravity of about 0.89, tensile strength of about 600 psi, and elongation of greater than about 1,000%. Alternatively, ChronoPrene™ 40A can be used, which has a Hardness-Shore A ASTM D2240 (3 sec.) rating of about 40, a specific gravity of about 0.90, tensile strength of about 700 psi, and elongation of about 500%. The material 26 may be pre-stretched or otherwise mechanically and/or thermally manipulated to improve performance.

In forming balloon 20, material 26 can be shaped into a tubular form and subjected to pre-treatment, which may include stretching and heating and annealing. The tube can then be bonded to tubular body 34. Bonding is preferably effected using adhesives, or using heat treatment, for example using laser, direct contact heat application, or forced air heating. Bonding can also be effected ultrasonically, or by RF (radio frequency) welding, or mechanically swaging or pinching, or by other techniques. In this manner material 26 is sealed against tubular body 34, or against retainers 36a and 38a, at regions 50 and 52, such that fluid-tight chamber 28 is achieved.

Designing the balloon 20 to be relatively large in length will compensate for any shortcomings arising from its relative softness and compliancy, and its low impact design. Larger size, in terms of the diameter of the balloon 20 when inflated and in terms of the overall length of the balloon is contemplated. A preferred balloon length range is about 4 mm to about 30 mm, and a more preferred balloon length range is about 7 mm to about 20 mm. A preferred balloon diameter range is about 1.5 mm to about 10 mm, and a more preferred balloon diameter range is about 3 mm to about 7 mm. A preferred length-to-diameter ratio range is about 0.5:1 to about 5:1. In this manner the balloon will effectively occlude/impede blood flow due to its large size, and particularly, large surface area, and will not need to rely on forming a tight seal over a small contact area with the blood vessel. Thus minimal stress is exerted against the vessel.

Balloon 20 is constructed such that an inflation pressure of about 200 mmHg, or about 3/10 atmosphere, will provide the necessary volume and force for proper operation. Such pressure will thus be slightly greater than systolic pressure, and will be just sufficient to inflate balloon 20 without causing appreciable deformation of the vessel. Accordingly, damage to the vessel tissue is minimized. It is however contemplated that pressures to about 600 mmHg are possible. Application of embolizing agent can take place when the vessel and aneurysmal sac are in their true shape and form, uninfluenced by straightening or mis-shaping forces. This will ensure that the introduced material is retained in place, without imparting prolonged stress to the region. Acceptable performance using ChronoPrene™ 15A has been realized, although ChronoPrene™ in the range of 5A to 25A can also be used.

It is also contemplated that balloon 20 is predisposed to take on certain irregular shapes matching those of the vasculature in which it is to be introduced. The balloon thus can be provided with nodules, or pre-stretched or pre-oriented during fabrication to take on these irregular shapes, for example to bulge or self-position in a particular direction, as seen in FIG. 1, with balloon 20 bulging to the left, into branch B of vessel 14.

The distal portion of catheter 10 is preferably relatively flexible in order to facilitate introduction of the catheter into tortuous vasculature. Other portions of catheter 10, however, may be relatively stiffer, in order to increase column strength and enhance pushability, thereby further facilitating control of the catheter. Relative stiffness may be achieved in a variety of ways, including suitable material selection, reinforcement, and so forth.

While described in the context of embolization procedures, it will be appreciated that the catheter and method of the invention are generally useful for occluding and/or impeding flow in any vasculature whose structural integrity has been compromised, since the invention involves minimal pressure and exertion of force against the vascular tissue, and will therefore not exacerbate the condition of the vessel.

The above are exemplary modes of carrying out the invention and are not intended to be limiting. It will be apparent to those of ordinary skill in the art that modifications thereto can be made without departure from the spirit and scope of the invention as set forth in the following claims.

What is claimed is:

1. A catheter suitable for use in a complex vessel comprising:
   a substantially tubular structure having at least one lumen; and
   a single compliant inflatable balloon located at a distal portion of said tubular structure and in fluid communication with said lumen,
   wherein at least a portion of said inflatable balloon comprises a material which is based on styrenic olefinic rubber and hydrogenated isoprene having a durometer hardness of 5 Shore A to 25 Shore A and is pre-stretched or mechanically or thermally manipulated during fabrication to take on the irregular shapes matching those of a vessel to which it is to be introduced; and further wherein, when the balloon is inflated, conforms to the shape of the vessel for a sufficient length of the vessel to attenuate and/or occlude blood flow therein and still further wherein the catheter does not significantly deform the vessel when fully inflated.

2. The catheter of claim 1, wherein the lumen is adapted to accommodate a guidewire therein.

3. The catheter of claim 1, where in the balloon material has a modulus at about 300% having a value less than about 300 psi and/or a tensile strength of about 600 psi.

4. The catheter of claim 1, wherein the balloon material has a Hardness-Shore A ASTM D2240 (3 sec.) rating of about 15, a specific gravity of about 0.89, tensile strength of about 600 psi, and elongation of greater than about 1,000%.

5. The catheter of claim 1, wherein the length of the balloon when inflated is about 4 mm to about 30 mm.

6. The catheter of claim 1, wherein the length of the balloon when inflated is about 7 mm to about 20 mm.

7. The catheter of claim 1, wherein the diameter of the balloon when inflated is about 1.5 mm to about 10 mm.

8. The catheter of claim 1, wherein the diameter of the balloon when inflated is about 3 mm to about 7 mm.

9. The catheter of claim 1, wherein the length-to-diameter ratio of the balloon when inflated is about 0.5:1 to about 5:1.

10. The catheter of claim 1, wherein the balloon is inflated to conform to the shape of the vessel at a pressure which is slightly greater than systolic pressure.

11. The catheter of claim 1, wherein the balloon is inflated to conform to the shape of the vessel at a pressure of up to about 600 mmHg.

12. The catheter of claim 1, wherein the balloon is inflated to conform to the shape of the vessel at a pressure of about 200 mmHg.

13. The catheter of claim 1, wherein the substantially tubular structure includes multiple lumens.

14. The catheter of claim 1, further including one or more radiopaque marker bands disposed in the vicinity of the balloon.

15. The catheter of claim 1, wherein the thickness of the balloon material is about 0.004 inches to about 0.006 inches.

16. The catheter of claim 15, wherein the thickness of the balloon material is about 0.005 inches.

* * * * *